Figure 1:
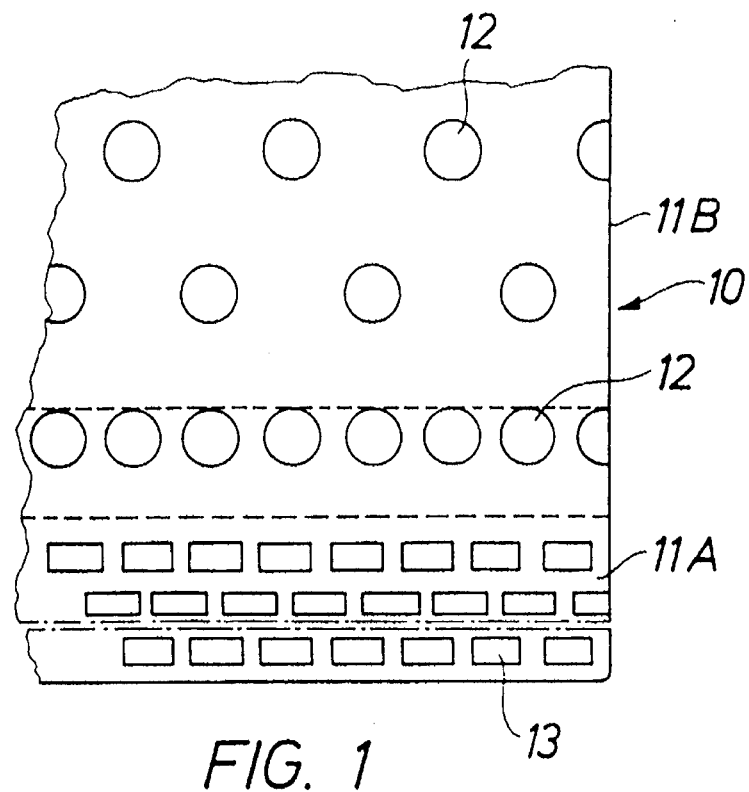

United States Patent [19]

Lundgren et al.

[11] Patent Number: 5,525,646
[45] Date of Patent: Jun. 11, 1996

[54] BIORESORBABLE MATERIAL AND AN ARTICLE OF MANUFACTURE MADE OF SUCH MATERIAL FOR MEDICAL USE

[76] Inventors: Dan Lundgren, Askims Kyrkväg 5, S-436 51 Hovås; Jan Gottlow, Klintasgatan 5, S-422 44 Hisings Backa; Torbjörn Mathisen, Bandhagsplan 9, S-132 24 Bandhagen, all of Sweden

[21] Appl. No.: 108,688

[22] PCT Filed: Mar. 4, 1992

[86] PCT No.: PCT/SE92/00139

§ 371 Date: Sep. 3, 1993

§ 102(e) Date: Sep. 3, 1993

[87] PCT Pub. No.: WO92/15340

PCT Pub. Date: Sep. 17, 1992

[30] Foreign Application Priority Data

Mar. 4, 1991 [SE] Sweden ................. 9100610

[51] Int. Cl.⁶ ............... A61F 2/00; C08K 5/10; C08G 63/91
[52] U.S. Cl. .......... 523/105; 523/115; 524/308; 524/310; 524/311; 525/410; 525/415; 525/461; 433/215; 433/201.1; 433/229; 424/423; 424/426; 623/12
[58] Field of Search .................. 523/105, 115; 433/215, 201.1, 202.1, 229; 424/423, 426; 525/410, 415, 461; 524/308, 310, 311; 623/11, 12

[56] References Cited

U.S. PATENT DOCUMENTS

5,061,281  10/1991  Mares et al. .................. 523/113

FOREIGN PATENT DOCUMENTS

| 0226061 | 6/1987 | European Pat. Off. . |
|---|---|---|
| 2406539 | 8/1975 | Germany . |
| 3635679 | 5/1988 | Germany . |
| 8804557 | 6/1988 | WIPO . |
| 9001521 | 2/1990 | WIPO . |
| 9007308 | 7/1990 | WIPO . |
| 9101126 | 2/1991 | WIPO . |

*Primary Examiner*—Paul R. Michl
*Assistant Examiner*—LaVonda R. DeWitt

[57] ABSTRACT

This invention relates to a bioresorbable material and an article of manufacture of such material for medical use comprising homopolymers, copolymers, or a blend thereof selected from the group of monomers including glycolic acid, lactic acid, caprolactone, trimethylene carbonate, para-dioxanone and 1,5 dioxepan-2-one, a plasticizer selected from the group including ethyl, butyl and hexyl esters of acetylated or non-acetylated citric acid, ethyl terminated oligomers of lactic acid, having no less than 2 and no more than 10 units, and lactic acid esters of glycerol, the material comprises 50% of amorphous polymer or polymers to impart to the material plastic malleability substantially without memory.

23 Claims, 4 Drawing Sheets

BIORESORBABLE MATERIAL AND AN ARTICLE OF MANUFACTURE MADE OF SUCH MATERIAL FOR MEDICAL USE

The present invention relates to a bioresorbable material and an article of manufacture made of such material for medical use to be implanted into a living organism, e.g. for selective influences on the healing process by guiding tissue growth, e.g. in healing after periodontal surgery (guided periodontal tissue regeneration) and in connection with regeneration of other hard and soft intra- and extra-oral tissues, the element preferably being in the form of an element, layer(s), foil, sheet or film, but the element may also be formed as a filament or tube.

During the last decades biodegradable materials have been increasingly widely used in the medical field. Initially collagen was introduced which, however, causes problems due to the fact that it has an irregular degradation time and may cause inflammatory and in some cases allergic reactions. Since the beginning of 1970 new materials with improved characteristics, in terms of biodegradation time and biocompatibility, have been developed, primarily polyglycolic acid (PGA) and polylactic acid (PLA). PGA and PLA have been successful commercially and are used today for medical applications, e.g. as sutures and orthopedic pins, applications where above all material strength is required.

The tissue regeneration applications mentioned in the introduction require another set of characteristics of the elements being used (aside from biodegradability and biocompatibility), primarily malleability at the time of surgery, and dimensional stability of the material during the healing phase after being implanted in vivo.

Malleability as used herein is a led-like plasticity, i.e. the material does not immediately or over a short period regain the shape that it had before it was reshaped, which means that the material has no or very little memory. Malleability according to this definition is important at the time of surgery so that the material can be located along the tissue to be covered and the shape of the material can be adapted to the shape of the region to be covered, often in a three-dimensional fashion. This characteristic facilitates the surgical procedure. Moreover, absence of a memory of the element assures that the adjacent tissue is exposed to a minimum of pressure.

Dimensional stability is important so that an appropriate design or shape imparted to the material can be maintained over a certain period of time which often can be defined as the period which is critical for the healing process. Dimensional stability reduces the tendency of the material to swell thereby eliminating a possible second source of pressure to the tissues adjacent to the implanted element.

WO 90/7308 describes several embodiments of an element for guiding tissue growth in regeneration of supporting tissues of teeth and dental implants, in healing after periapical operations, and in connection with filling of bone cavities caused by cysts and malformations, and diastases caused by bone fractures. In said application polymers are said to be suitable materials for the biodegradable element, and among others polylactide (PLA) is mentioned.

PLA can be pliable if woven or knitted but is hardly malleable. It is moreover very difficult if at all possible to make structures other than those inherent in the weaving or knitting techniques. By using other known manufacturing technique, such as compression molding, injection molding, or calendering among others, it is in fact possible to make small structures in PLA that are stable over a certain period, but such structures would not be malleable and would fracture easily due to the physical state of the PLA polymer itself. Polytrimethylene carbonate is a bioresorbable material which is soft but elastic rather than malleable, i.e. it will spring back when folded. Due to a low glass transition temperature this material has poor dimensional stability, and moreover, the bioresorption thereof extends over a long time, probably no less than two years, which could be a disadvantage, e.g. in the periodontal application, and has specific negative consequences, e.g. in the periodontal application where there is a connection between the bioresorbable element and the oral cavity with the consequent increased risk for infection.

WO 88/04557 describes implants of different kinds which have desired mechanical and physiological properties and in a living organism have an unexpected favourable influence on the cell growth and the tissue regeneration. These implants comprise at least one basic polymer component and at least one hydrophobic polymer component which is at least as hydrophobic as lactide. The material of these implants can comprise bioresorable polymers with a plasticizer added.

Plasticizers from the citrate ester family and triacetin have been in use to impart greater flexibility and suturability to nerve guidance tubes as mentioned in EP 0 226 061. These nerve guidance tubes are preferably made from poly-d,l-lactide but can also consist of polymers containing other α-hydroxy acids.

U.S. Pat. No. 4,961,707 describes a membrane for guided periodontal tissue regeneration made from a bioresorable material; among others poly lactic acid is mentioned, in which an additive may be incorporated. Among others, the additive could be a plasticizer from the citrate ester family.

U.S. Pat. No. 5,032,445 describes method and articles for treating periodontal desease and bone defects. When an article is used it should be made from a biocompatible, porous material selected from, among others, polycarboxylates and polyesters.

S. Yolles reports the use of tri-n-butyl citrate as a plasticizer for polylactic acid microspheres for sustained release of drugs (Yolles, S. Journal of Parenteral Drug Association, vol. 32(4), 188–191, 1978) and (Yolles, S.; Leafe, T.; Ward, L.; Boettner, F. Bulletin of the Parenteral Drug Association, vol. 30(6), 306–312, 1976). The only comment given regarding tri-n-butyl citrate is that it had a small effect on the release rate of the drug used.

E.W. Henry reports the use of 2 to 10% triethyl citrate to plasticize poly-d,l-lactide which was used among other materials to study the regneration of a damaged nerve by the use of tubes that protect the nerve ends during healing (Henry, E.W.; Chiu, T-H; Nyilas, E.; Brushart, T.M.; Dikkes, P.; Siedman, R.L.). Swelling of the material was recognized as a problem.

There is little or no information in the patent and scientific literature regarding the effect in terms of new properties obtained when a plasticizer is incorporated in the group of polymers commonly known as bioresorbable polymers, such as polymers, copolymers or blends thereof made from the group of monomers including glycolic acid, lactic acid, caprolactone, trimethylene carbonate, paradioxanone, and 1,5-dioxepan-2-one. These materials all have the characteristic that they are degraded by hydrolysis in the human body to harmless hydroxy acids or alcohols which can be metabolized or excreted. The hydrolysis occurs through out the bulk of a device made of such bioresorbable materials as mentioned above and more acidic and alcoholic end groups are formed from the hydrolysis, which create a more hydrophilic environment in the device. More water penetrates into the bulk of the device than degradation products are leaving the same, which can be observed as a weight increase of the device by gravimetric analysis. This absorbed water creates a force from the interior that acts on the device, causing it to swell, if the device has a low modulus of elasticity, characterised as soft, or to disintegrate if the modulus of elasticity is high, characterised as hard. The disintegration will then occur first when the mechanical strength of the device has been lowered, due to degradation, to such an extent that the internal force is higher than the tensile strength of the material of the device. Polymers made of glycolic acid, lactic acid, caprolactone and paradioxanone are all polymers with high modulus of elasticity, while polymers of trimethylene carbonate and 1,5-dioxepan-2-one are examples of polymers with low modulus of elasticity. The modulus can be changed by copolymerization or by blending the different polymers.

To reduce the modulus of elasticity a plasticizer can be added to the polymer. It is, however, necessary that the plasticizer is compatible with the polymer so that the plasticizer is evenly distributed in the polymer. The plasticizer acts in a way like a lubricant for the polymer chains and increases the mobility in the system. This may also increase the ability of water to penetrate into the bulk of a device made from such a plasticized material. The strength of the material in such an element will be lower than that of the unplasticized material and, therefore, the swelling will be more pronouned and in some instances so severe that the material will have no practical use.

The property of swelling for the above mentioned polymers is a natural consequence of hydrolysis and can not be hindered if one wants to have a resorbable material. When a plasticizer is added the swelling increases due to reduced mechanical strength of the plasticized material. Accordingly, only through careful selection of plasticizer and polymer, copolymer or blends thereof acceptable properties of a material to be used for a specific purpose can be achieved. The reason of incorporating a plasticizer, as found in some of the references cited above, has been to reduce the modulus of elasticity or to make an otherwise brittle material more flexible so that it can be bent or deformed without fracture. Polymers like poly-d,l-lactide or copolymers of lactide and glycolide are usually very brittle in their pure state. Plasticizers like citrate esters have little or no effect on the rate of resorption of the polymers mentioned above. However, the plasticizer triacetin has such an effect which may be explained by its rapid hydrolysis to glycerol and acetic acid. The liberated acerid acid may act as a catalyst for the hydrolysis of the polymer.

The term internal plasticization is often used for systems when two monomers whose homopolymers have different glass transition temperatures (Tg) are copolymerized. Normally one polymer has a low Tg and the other a high Tg like poly-trimethylene carbonate (PTMC), Tg being approximately −18° C., and poly-d,l-lactide (d,l-PLA), Tg being approximately 57° C. The copolymer made from these monomers will have a Tg ranging from −18° to 57° C. depending on the ratio of the two monomers. Internal plasticization of poly-d,l-lactide can thus be achieved by incorporating trimethylene carbonate into the chain. For example, a monomer ratio of 70/30 between d,l-lactide and trimethylene carbonate (TMC) yields a copolymer with Tg approximately 25° C. The same effect of internal plasticization can be achieved by the use of caprolactone instead of TMC as the comonomer. Such polymers are described by S.J. Hanson et al (Hanson, S.J.; Jamshidi, K; Eberhart, R.C. Trans. Am. Soc. Intern. Organs, vol. XXXIV, 789–793, 1988) for evaluation of their potential use as vacular grafts and in GB 8918343 as a material than can be used for periodontal regeneration. This patent application demonstrates both the lowering of Tg and the reduction in modulus of elasticity as a consequence of internal plasticization. 1,5-dioxepan-2-one which yields upon polymerization a homopolymer with Tg of −39° C., according to Mathisen et al (Mathisen, T.; Masus, K; Albertsson, A.C. Macromolecules, 22, 3842–3846, 1989), can furthermore be copolymerized with lactides or glycolides to yield a material with the same effect of internal plasticization as that mentioned above.

However, only the term reduction of the modulus of elasticity is often not enough to express the property often desired in an element for surgical application. Certain cross linked rubbers like silicones or polyurethanes, characterized by low hardness, 30–80 Shore A, feel very soft and have a low modulus of elasticity but have a high memory. All polymeric materials have the unique time dependent property called visco elasticity, which means that upon release of a non permanent deforming load the material will eventually regain its shape. If the material was purely elastic it would immediately retain its shape. For visco elastic materials it will take a certain time to regain the shape depending on the polymer the material is made of. Some materials may not fully regain their shape and are said to be plastically deformed, deformation occuring without rupture.

The cross linked rubbers mentioned above, silicones and polyurethanes, cannot be plastically deformed by small forces due to their cross links which remember what the device looked like when the cross links were formed. These materials have a memory and always return to their original shape after the load has been released unless the material ruptures during deformation. The internal plasticized copolymers mentioned above also have a high degree of memory even though they may have a low modules of elasticity. Plasticizing these copolymers further with low molecular weight molecules compatible with the copolymer will decrease the viscosity and thus reduce the memory in the system consisting of the plasticizer and the copolymer. This means that the time to regain the original shape increases after release of a small load. Such low molecular weight molecules, referred to as plasticizers, may be, but are not limited to, ethyl butyl, and hexyl esters of acetylated or non-acetylated citric acid, ethyl terminated oligomers of lactic acid, wherein the number of lactic acid units ranges from 2 to 10, and lactic acid esters of glycerol. These plasticizers act in the same way in order to plasticize homopolymers such as the amorphous poly-d,l-lactide or the amorphous copolymers of glycolide and lactide. By incorporating the plasticizer in a correct ratio which depends on the properties of the polymer, copolymer or blends thereof, a material with very little momory or a led-like plasticity can be achieved. This makes the material malleable, which means that it is easy to deform and shape.

From what has been said above about bioresorbable polymers and plasticization of such polymers, it is clear that increased malleability in such materials only can be achieved at the expense of increased swelling and, consequently, impaired dimensional stability. During recent years, however, there has arisen an increased demand of bioresorbable materials and elements that strike an advantageous balance between malleability and dimensional stability.

The purpose of the present invention is to provide a bioresorbable and biocompatible element which combines malleability and dimensional stability so as to be advantageous in tissue regeneration and guiding applications.

In order to achieve said purpose the material of the invention has obtained the characterizing features of claim 21.

The article of manufacture has obtained the characterizing features of claim 12.

The inventors have found that the components should be combined in such a way as to make the material substantially malleable and substantially permanent in the shape imparted thereto without significant spring back. In other words, the material should lack or have marginal memory function so as to be more easily handled when it is to be implanted into the organism, the material at the same time being more compatible with surrounding tissue; a material which springs back can irritate or cut through surrounding tissue and may be difficult to handle practically at the surgery.

To impart to an element the property of having plastic malleability substantially without memory the proportion plasticizer should be of the order ranging from 5 to 25% by weight. The optimum varies depending on the composition of the polymer. The optimum falls between 9 and 17% by weight if the polymer is based on PLA and the plasticizer is based on citrate esters; it is around 20% by weight with the same polymer but with ethyl terminated lactic acid oligomers as the plasticizer agent. It must be understood that the bending module of a rectangular bar is dependent on the third power of the thickness of the bar. That means that a thick bar will feel more stiff than a thin bar and therefore need more force to be deformed. Thicker elements therefore may need more plasticizer added than thinner elements in order for the elements to have the same malleability. The figures of plasticizers above correspond to an element having a thickness in the range of 30 μm to 1000 μm and preferably in the range from 50 to 150 μm.

The major component in the material should be an amorphous polymer such as but not limited to poly-d,l-lactide, amorphous copolymers such as poly lactide-co-glycolide, poly lactide-co-trimethylene carbonate, poly glycolide-co-trimethylene carbonate, poly-lactide-co-caprolactone, poly glycolide-co-caprolactone, poly lactide-co-1,5-dioxepan-2-one, poly glycolide-co-1,5- dioxepan-2-one, and any blends thereof that is compatible with the plasticizer in order to achieve a homogenous blend and to impart to the element an acceptable plastic malleability.

The material compositions include compositions that are suitable as vehicles for the delivery of biochemical substances, e.g. antibiotics such as tetra and minicycline, antiseptics such as clorhexidine, and growth stimulating substances such as Transforming Growth Factor beta, Insulin-like Growth Factor 1, Insulin-like Growth Factor 2, Platelet Derived Growth Factor and Bonemorphogenic Growth Protein.

By the polymer mixture having been plasticized in order to impart to the material the intended malleability, the material will, however, absorb water and such absorption causes swelling of the material to a degree which varies depending on the type of plasticizer used and the concentration thereof. In order to envision the relationship between the swelling of such plasticized polymers and the properties of the plasticizer and polymer itself several mixtures where made in order to quantity the swelling of such blends. The following is a short general description of how the polymer plasticizer blends were made.

Approximately 25 g of polymer and plasticizer were dissolved in 250 ml of methylene chloride in order to obtain a homogeneous solution. The solution was placed in a cupboard overnight in order to allow most of the solvent to evaporate in order to form a polymer film of the mixture. The polymer film was transferred to a vacuum oven, and a vacuum of 1 mbar or less was applied. After 24 hours the temperature in the oven was raised to 60° C. and the film was left under this condition for 9 days. This vacuum dried film was then compression molded into a thin sheet with a thickness of 0.2 mm. From this sheet circular test samples 10 mm in diameter were punched out and used for the determination of swelling.

The swelling was determined by exactly measuring the thickness of each test sample both prior to and after ageing in a saline phosphate buffer solution, pH 7.4. The samples were incubated at 37° C. during the test. Measuring of thickness was performed by the use of a dial gauge.

TABLE 1

| Composition | Change in thickness, % | |
|---|---|---|
| | 10 days | 20 days |
| d,l-PLA i.v. 0.8 | 1 | 2 |
| 90 wt-% d,l-PLA i.v. 0.8/10 wt-% TEC | 8 | 30 |
| 90 wt-% d,l-PLA i.v. 1.5/10 wt-% TEC | 5 | 10 |
| 85 wt-% d,l-PLA i.v. 0.5/15 wt-% TEC | 63 | 105 |
| 85 wt-% d,l-PLA i.v. 0.8/15 wt-% TEC | 10 | 31 |
| 85 wt-% d,l-PLA i.v. 1.5/15 wt-% TEC | 8 | 13 |
| 90 wt-% d,l-PLA i.v. 0.8/10 wt-% TBC | 2 | 8 |
| 90 wt-% d,l-PLA i.v. 1.5/10 wt-% TBC | 3 | 9 |
| 85 wt-% d,l-PLA i.v. 1.5/15 wt-% TBC | 6 | 16 |
| 90 wt-% d,l-PLA i.v. 0.8/10 wt-% ATBC | 1 | 3 |
| 90 wt-% d,l-PLA i.v. 1.5/10 wt-% ATBC | 4 | 7 |
| 85 wt-% d,l-PLA i.v. 0.8/15 wt-% ATBC | 2 | 6 |
| 85 wt-% d,l-PLA i.v. 1.5/15 wt-% ATBC | 3 | 15 |
| 85 wt-% d,l-PLA i.v. 0.8/15 wt-% ETL | 16 | 21 |
| 85 wt-% d,l-PLA i.v. 1.5/15 wt-% ETL | 6 | 8 |
| 80 wt-% d,l-PLA i.v. 0.5/20 wt-% ETL | 49 | 95 |
| 80 wt-% d,l-PLA i.v. 0.8/20 wt-% ETL | 15 | 40 |
| 80 wt-% d,l-PLA i.v. 1.5/20 wt-% ETL | 4 | 12 | d,l-PLA = Poly-d,l-lactide
TEC = Triethyl citrate
TBC = Tributyl citrate
ATBC = Acetyltri butyl citrate
ETL = Ethyl terminated oligomer of lactic acid, mainly trimer.
i.v. Inherent viscosity Table 1 above shows some of the polymer—plasticizer combinations of a two component system and their ability to swell after 10 and 20 days of incubation of the buffer solution. As can be seen, the swelling behaviour depends on the molecular weight of the base polymer, in this case poly-d,l-lactide, the content of plasticizer as well as the type of plasticizer. It can generally be seen that water soluble plasticizers like TEC tend to swell the polymeric material more than a water-insoluble plasticizer such as ATBC does. Increase in the molecular weight of poly-d,l-lactide increases he swelling when the plasticizer is ATBC while the opposite is true for TEC as the plasticizer. At present there is no explanation for this behaviour.

TABLE 2

| Composition | Change of thickness, % | |
|---|---|---|
| 90 wt-% d,l-PLA i.v. 0.8/5 wt-% PCL/5 wt-% ATBC | 4 | 5 |
| 75 wt-% d,l-PLA i.v. 0.8/20 wt-% PCL/5 wt-% ATBC | 3 | 7 |
| 81 wt-% d,l-PLA i.v. 0.8/9 wt-% l-PLA/10 wt-% ATBC | 4 | 6 |
| 81 wt-% d,l-PLA i.v. 1.5/9 wt-% l-PLA/10 wt-% ATBC | 6 | 6 |
| 76 wt-% d,l-PLA i.v. 0.8/9 wt-% l-PLA/50 wt-% ATBC | 4 | 6 |
| 76 wt-% d,l-PLA i.v. 1.5/9 wt-% l-PLA/15 wt-% ATBC | 3 | 3 |

TABLE 2-continued

| Composition | Change of thickness, % | |
|---|---|---|
| 40 wt-% d,l-PLA i.v. 0.8/60 wt-% PTMC | 0 | 1 |
| 60 wt-% d,l-PLA i.v. 0.8/40 wt-% PTMC | 1 | 3 |
| 80 wt-% d,l-PLA i.v. 0.8/20 wt-% PTMC | 3 | 4 |
| 76 wt-% d,l-PLA i.v. 0.8/9 wt-% PTMC/15 wt-% ATBC | 3 | 10 |
| 72 wt-% d,l-PLA i.v. 0.8/18 wt-% PTMC/10 wt-% ATBC | 6 | 15 |
| 76 wt-% d,l-PLA i.v. 0.8/9 wt-% PTMC/15 wt-% ETL | 4 | 10 |
| 66 wt-% d,l-PLA i.v. 0.8/19 wt-% PTMC/15 wt-% ETL | 6 | 13 | d,l-PLA = Poly-d,l-lactide
PCL = Poly-caprolactone
l-PLA = Poly-l-lactide
PTMC = Poly-trimethylene carbonate
ATBC = Acetyltri butyl citrate
ETL = Ethyl terminated oligomer of lactic acid, mainly trimer.
i.v. = Inherent viscosity.

Table 2 shows examples of swelling of materials composed of a three component system, that is two polymers and one plasticizer. Table 2 only shows blends of polymers but amorphous copolymers which have been mentioned earlier when discussing internal plasticization could as well have been used as the base polymer rather than poly-d,l-lactide. As can be seen the swelling is drastically reduced by the introduction of a small amount of a crystalline polymer like poly-l-lactide and poly-caprolactone and polydioxanone. Also the more hydrophobic poly trimethylene carbonate has the ability to reduce the swelling but not to such an extent.

As can be seen from Table 1 and 2 the swelling can be up to 100% and in some cases even up to 200% measures as thickness increase, especially for copolymers of glycolide and lactide plasticized with water soluble plasticizers such as TEC or triacetin. In the human body or in vitro the swelling may be magnitudes higher and no easy correlation has been found so that dimensional changes can be accurately predicted for an element implanted in vivo. In vivo studies indicate possible swelling of 300% and more for certain combinations of plasticizer and copolymer like for instance low molecular weight poly-d,l-lactide plasticized with 14 wt-% TEC. Often the swelling has a negative biological influence by forcing an increased pressure on the surrounding tissue, which e.g. in the periodontal application can cause rupture of a repositioned flap. The swelling will, furthermore, impair the dimensional stability of the material and thereby jeopardizing those structures, if any, that an element made of the material may have been provided with, such as pores, perforations, depressions, ribs, grooves or spacers. In order to minimize the swelling of such an element while maintaining the malleability thereof the inventors have found techniques to augment the stability of the material thus minimizing the tendency of the material to swell.

To reduce drastically the tendency of swelling of the plasticized polymer, the element made of the material of the invention is perforated. This allows tissue ingrowth into the perforation apertures, resulting in firm integration of the element at the surgical site. In-vivo studies clearly indicate that the pressure on the layers of the element from such integrated tissue is higher than the pressure caused by the inflow of water into the element, swelling of the element thus being counteracted. The perforation apertures must be sufficiently large for the tissue integration to take place before the time of the exponential-like increase of the dimensions of the element. The time of occurrence of this event varies depending on the material composition but typically takes place at around 20–30 days in relatively stable compositions. Furthermore, the perforation apertures must be positioned close to each other on the element.

To be effective the individual apertures as well as the total aperture area ("transparency") of the element must have a minimum size. The individual perforations must be at least 10 μm in diameter. This is necessary for cells to grow through the perforation accompanied by a sufficient volume of collagen tissue to achieve the intended timely integration between tissues from both sides of the element. The "transparency" of a layer on an element should probably be at least 6%. The intended integration will be accomplished faster if the "transparency" and the aperture size is larger. Thus an element or a layer of the material of the invention will swell less with a larger area covered by apertures. The upper limit of the "transparency" and aperture size (transverse dimension) is limited by mechanical properties of the material and the intended function of the element. It also is preferable that the apertures be spaced at a center to center distance ranging from about 700 μm to 150 μm.

It is favourable in order to augment the dimensional stability to include a portion of a crystalline polymer into the composition, between 5 and 40% by weight depending on the level of stability requested.

Examples of compositions (by weight) are:
1) 76% poly-d,l-lactide, 10 % poly-l-lactide and 14% acetyltri-n-butyl citrate (ATBC).
2) 75% poly-d,l-lactide, 10% poly-caprolactone and 15% ATBC.
3) 80 % poly-d,l-lactide and 20% ethyl terminated oligomer of lactic acid.

Although the perforation has been found to be particularly advantageous in connection with elements consisting of the compositions of the invention, the inventors are aware of the fact that such perforations may be advantageous in augmenting the stability of other polymers that are used in biodegradable and biocompatible elements not demonstrating the specific malleability of the material proposed according to the invention, and also for other applications than those referred to herein.

Figure 2:
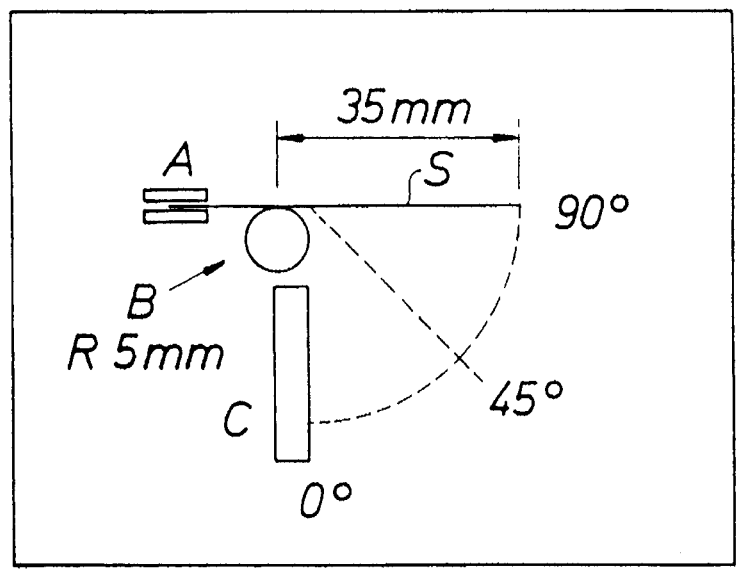
Figure 3:
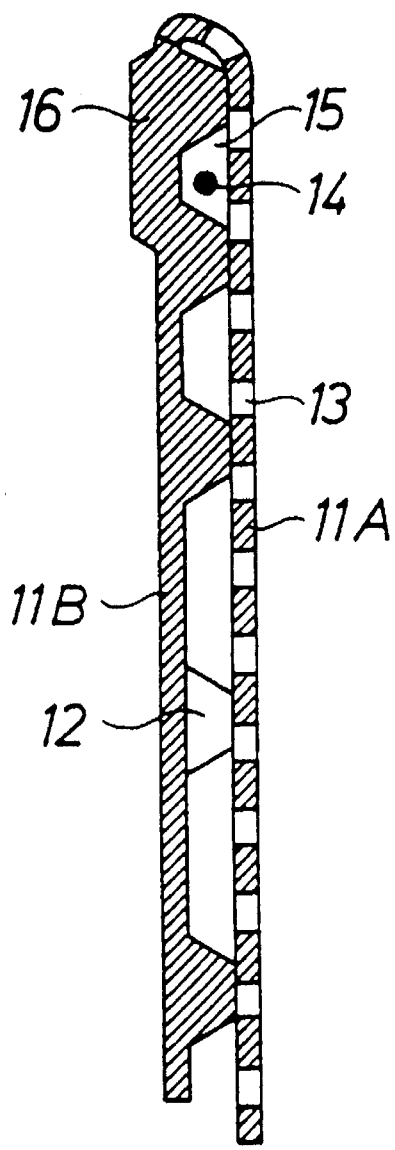
Figure 4:
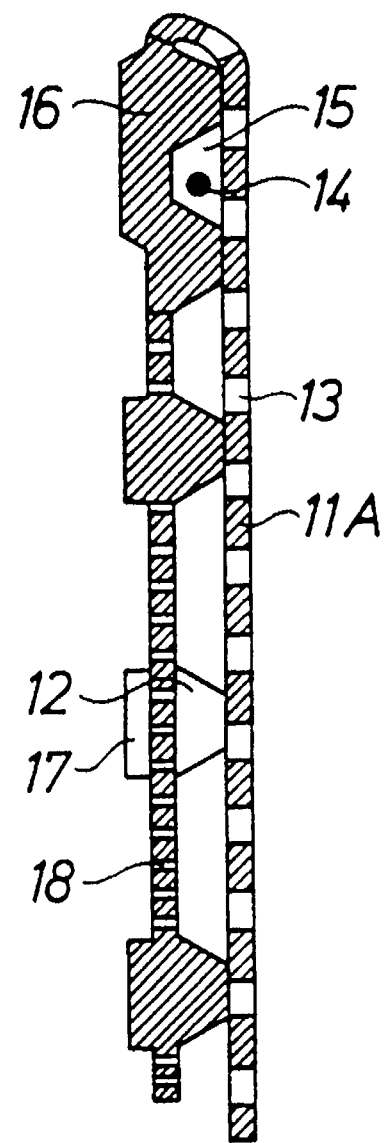
Figure 5:
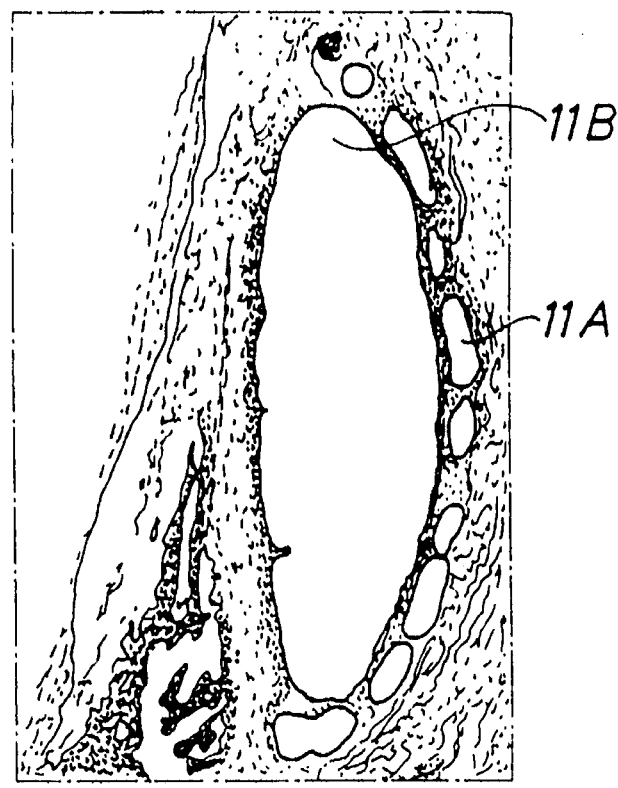
Figure 6:
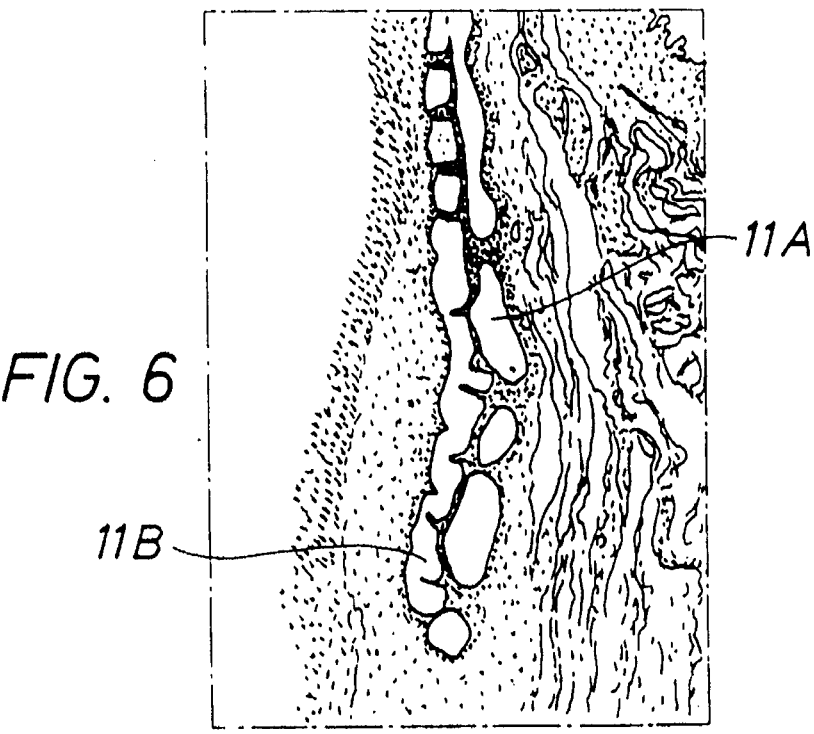
Figure 7:
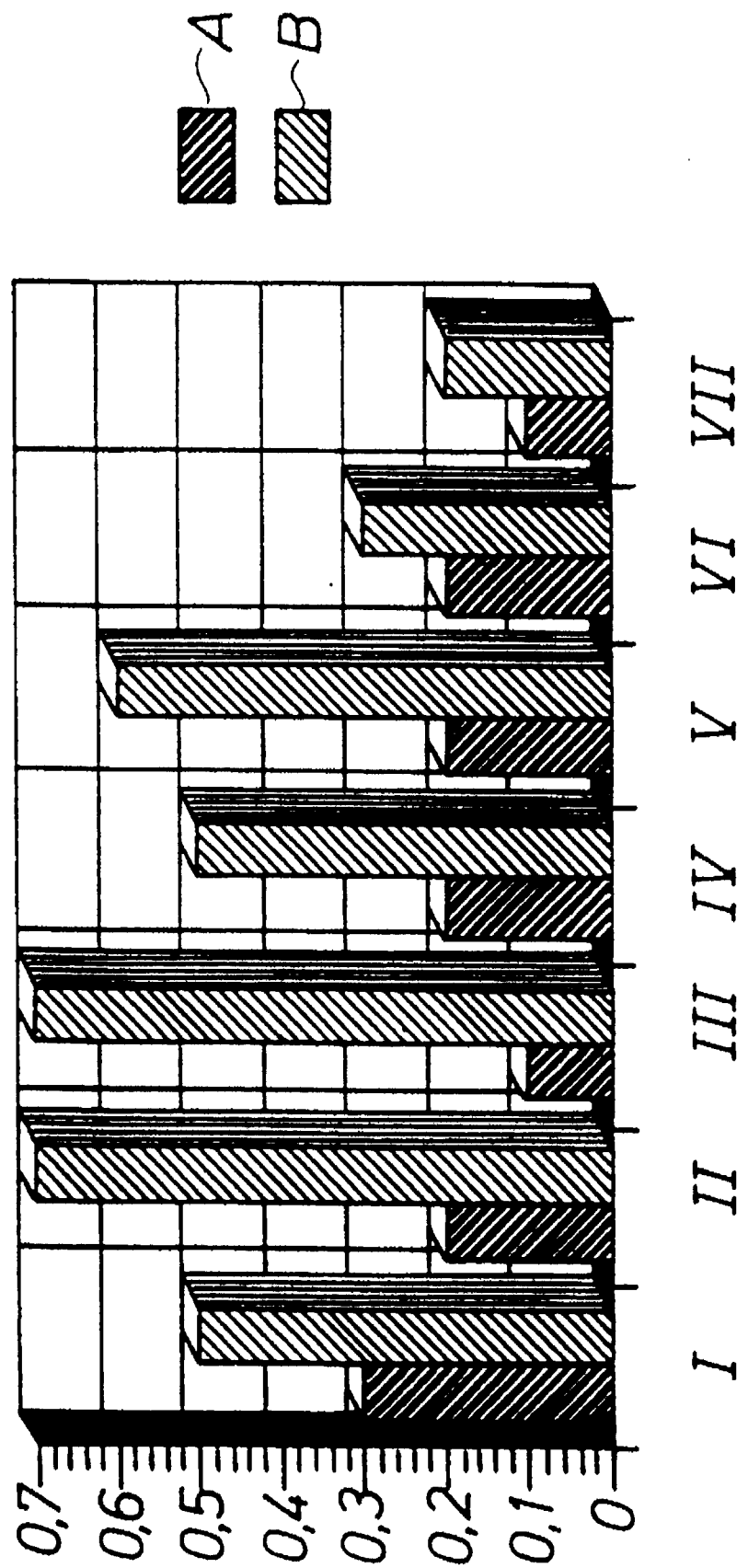

In order to explain the invention in more detail embodiments thereof will be described below, reference being made to the accompanying drawings in which FIG. 1 is a plan view of an element of the material of the invention in one embodiment thereof, FIG. 2 is a diagrammatic view of an apparatus for measuring the plastic malleability;

FIG. 3 is a cross-sectional view of the element in FIG. 1,

FIG. 4 is a view similar to that of FIG. 3, showing another embodiment of the element having spacers on one side of the double-wall structure, FIGS. 5 and 6 are histological pictures disclosing the importance of the perforation in reducing swelling of the material, and FIG. 7 is a comparative diagram showing the swelling of an element of the material of the invention with and without perforation, respectively.

The elements disclosed in the drawings are both of the type described in WO 90/07308 with reference to FIGS. 21 and 22 therein and comprise a sandwich structure made of a rectangular blank 10 having two substantially equal portions 11A and 11B shown fragmentarily only in FIG. 1. This blank is a foil having a thickness e.g. of about 100 μm and is e.g. of the size 10×20 mm. The blank is made of the polymer material of the invention and more particularly of a polylactide with plasticizer and was prepared as follows:

A mixture (example 1 mentioned above) comprising 37,5 g poly-d,l-lactide 5 g poly-l-lactide 7,5 g acetyltri-n-butyl citrate (ATBC) (plasticizer) were dissolved in 500 ml methylenechloride in order to get a homogeneous solution. The solution was placed in a cupboard overnight in order to allow most of the solvent to evaporate in order to form a polymer film of the mixture. The polymer film was transferred to a vacuum oven, and a vacuum of 1 mbar or less was applied. After one day the temperature in the oven was raised to 60° C. and the film was left under this condition for 9 days.

The material thus produced has plastic malleability substantially without memory. The marginal memory function or very little memory of a material can be defined by using the time for an element of such material to regain shape after deformation by a small load, hereinafter denoted recovery time. To standardize such a measurement of recovery time a simple apparatus as shown in FIG. 2 can be used. A strip 10 mm wide, 55 mm in length and 0.2±0.005 mm in thickness is used for the test. The specimens is clamped between two metal jaws at A so that the sample touches the periphery of a cylinder B. As seen in FIG. 2 the length of the free hanging test sample from the point it touches the cylinder and out shall be 35 mm. When the specimen has been clamped in the correct fashion it is gently folded around the cylinder B and further down to a resting plate C where the specimen is hold against this plate for 10 seconds before it is released. The specimen will then start to regain its original shape as a linear non-bent specimen. A polyuretane or silicone rubber will immediately regain its shape in a shap-back fashin with no permanent bend. This means that recovery time is so small that it is not measurable. For plasticized polymers as mentioned above the time for recovery will vary depending on the polymer and the plasticizer used. A definition of a material having plastic malleability substantially without memory will in this test have recovery time of more than 5 seconds for the bend to be reduced from initial 90 degrees to 45 degrees. It is understood that the test is performed in an environment with 30° C. The specimen must be conditioned in this atmosphere 24 hours before being tested.

The blank 10 of FIG. 1 was produced by compression molding, but other manufacturing methods can be applied such as callendering, casting, molding, or other techniques. Portion 11B forms at one side thereof protrusions 12 which have the shape of truncated cones with a base diameter of about 0.4 mm and a height of about 0.2 mm. The protrusions of one row thereof adjacent portion 11A have a center distance of about 0.6 mm, and the center distance of the remaining rows being about 1.2 mm and the center distance between the rows being about 1.0 mm.

When a bioresorbable polymer is mixed with a plasticizer there is a problem with swelling due to increased absorption of water in the material as a consequence of the plasticizer having been added. The swelling may be of the order of 300%. By this swelling the blank made of the material may disrupt and the element may cause pressure on adjacent tissues with possible negative consequences, as mentioned above. The swelling problem can be limited by combining components that impart to the material some hydrophobicity so as to limit the water absorption, and crystallinity so as to improve the strength of the material. However, the swelling can also be reduced by perforation of the element, and such perforation has been found in vivo to reduce swelling substantially. This method of reducing swelling is applied to the blank 10 manufactured as described above by treating the blank in order to perforate the portion 11A. The perforation apertures 13 are rectangular in shape 0.2×0.4 mm and the center distance between the apertures in each row is about 0.5 mm and between the rows about 0.35 mm. The apertures cover about 40% of the surface area of portion 11A.

As shown in FIG. 3 the blank of FIG. 1 has been folded to form a double-wall structure or laminate wherein the adjacent surfaces of portions 11A and 11B are spaced by the protrusions 12 at a distance of 0.2 mm to create a free space between the surfaces. The protrusions 12 forming spacers between portions 11A and 11B are glued to portion 11A. The glue used is a mixture of 17% by weight of poly-d,l-lactide and 3% by weight acetyltri-n-butyl citrate in ethyl acetate forming the rest of the mixture.

A suture 14 for tying the sandwich type element of FIG. 2 to a tooth with the smooth outside surface of portion 11B facing the tooth is located in a space 15 defined between portions 11A and 11B by a rib or bar 16 extending over the full width of portion 11B and protruding at both sides thereof, and the adjacent protrusions 12, to be used.

In the modified embodiment disclosed in FIG. 4 the portion 11B forms at the outside surface thereof protrusions 17 distributed over the surface in the same configuration as protrusions 12 and having a height of about 0.1 mm. These protrusions are provided to form spacers between the outside surface of portion 11B and the surface of the tooth. Moreover, there are provided small circular apertures 18 having a typical diameter of 80 m and arranged in a hexagonal pattern wherein the center distance of the apertures is about 0.2 mm. These apertures cover an area of about 15% of the surface area.

Elements of the two types described above have been implanted in periodontal defects around teeth in the oral cavity of monkeys (Macaca Fascicularis). In the experimental model an incision was made and a mucoperiosteal flap was raised to expose the bone, which was resected to surgically create a recession-type defect. The element was cut to shape to fit the profile of the defect. Using the attached suture 14, the element then was tied to the tooth in the cemento-enamel region, so that the element completely covered the defect. The flap was repositioned and secured with sutures to cover the element and defect area.

The monkeys were given antibiotics at the time of surgery. Plaque control was maintained by topical application on teeth and surrounding gingiva, once a week, of a chlorhexidine solution. The monkeys were sacrificed 4 and 6 weeks after surgery. Following sacrifice, the jaws were removed and specimens containing the experimental teeth and their periodontal tissues were dissected and placed in a solution of 10% buffered formalin. The specimens were decalcified in EDTA, dehydrated and embedded in paraffin. Bucco-lingual sections of each specimen were prepared with the microtome. The sections were stained with hematoxylin eosin or Mallory's connective tissue stain. From each root sections were used for microscopic analysis.

In all elements of the FIG. 3 embodiment, i.e. without apertures in portion 11B facing the root surface, a severe swelling of the element could be noticed, typically from 140 µm to 600 µm or, expressed in percentage of the initial thickness of the element before implantation, the swelling was of the order of 300% or more. In portion 11A having the rectangular apertures 13 the order of swelling was 60%. For elements of the FIG. 4 embodiment having apertures 16 in portion 11B the magnitude of the swelling was about 60% for both portions 11A and 11B.

FIG. 5 illustrates the swelling of an element of the type shown in FIG. 3 such swelling occurring in portion 11B while portion 11A is uneffectd by swelling, and the substantially reduced swelling of such material when perforated, marked by solid arrows. FIG. 6 shows an element of the type shown in FIG. 4 made of the same material as the element in FIG. 5 and having perforation in both layers. This figure demonstrates substantially reduced or substantially eliminated swelling of portion 11B.

The diagram in FIG. 7 finally illustrates the results of measurements made on elements according to FIGS. 3 and 4 of the material of the invention columns A referring to portion 11A and columns B referring to portion 11B. The columns represent the measured width of said portions. The vertical axis indicates the measures width in mm, and the horizontal axis indicates the type of perforation used according to the table 3 below:

TABLE 3

| Type | Membrane | Perforation | Transparency % |
|------|----------|-------------|----------------|
| I | Portion 11A | Circular aperture diameter 200 μm | 15 |
|  | Portion 11B | Unperforated |  |
| II | Portion 11A | Circular aperture diameter 300 μm | 31 |
|  | Portion 11B | Unperforated |  |
| III | Portion 11A | Circular aperture diameter 300 μm | 51 |
|  | Portion 11B | Unperforated |  |
| IV | Portion 11A | Rectangular aperture 200 × 400 μm | 31 |
|  | Portion 11B | Unperforated |  |
| V | Portion 11A | Rectangular aperture 200 × 400 μm | 41 |
|  | Portion 11B | Unperforated |  |
| VI | Portion 11A | Circular aperture diameter 300 μm | 30 |
|  | Portion 11B | Circular aperture diameter 60 μm | 25 |
| VII | Portion 11A | Rectangular aperture 200 × 400 μm | 41 |
|  | Portion 11B | Circular aperture diameter 300 μm | 50 |

The material of the elements was that specified in example 1 above.

These findings clearly indicate a close relationship between a perforated element and the dimensional stability thereof when made of a plasticized polylactide. The factor responsible for the increase of the dimensional stability clearly depends on the shape of the perforation apertures and on the size and number of the perforation apertures. The optimum may vary for an element of one, two or more layers or for elements of different configurations as earlier referred to.

We claim:

1. Bioresorbable material adaptable for medical use comprising:

bioresorbable polymer comprising at least one amorphous polymer or copolymer selected from the group consisting of poly-d,l-lactide, and copolymers of poly-d,l-lactide and polycaprolactone, poly-l-lactide, or polytrimethylene carbonate, said amorphous polymer comprising at least 50% by weight of said material;

at least one crystalline polymer selected from the group consisting of poly-l-lactide, polycaprolactone and polydioxanone; and a plasticizer selected from the group consisting of ethyl, butyl and hexyl esters of acetylated citric acid, and ethyl-terminated oligomers of lactic acid having no less than 2 and no more than 10 units of lactic acid;

said material being characterized by having plastic malleability substantially without memory combined with low swelling.

2. An article of manufacture adaptable for medical use made from a bioresorbable material comprising:

bioresorbable polymer comprising at least one amorphous polymer or copolymer selected from the group consisting of poly-d,l-lactide, and copolymers of poly-d,l-lactide and polycaprolactone, poly-l-lactide, or polytrimethylene carbonate, said amorphous polymer comprising at least 50% by weight of said material;

at least one crystalline polymer selected from the group consisting of poly-l-lactide, polycaprolactone and polydioxanone; and a plasticizer selected from the group consisting of ethyl, butyl and hexyl esters of acetylated citric acid, and ethyl-terminated oligomers of lactic acid having no less than 2 and no more than  l units of lactic acid;

said material being characterized by having plastic malleability substantially without memory combined with low swelling.

3. A bioresorbable material adaptable for medical use comprising:

bioresorbable polymer comprising at least one amorphous polymer or copolymer selected from the group consisting of poly-d,l-lactide, and copolymers of poly-d,l-lactide and polycaprolactone, poly-l-lactide, or polytrimethylene carbonate;

and a plasticizer based on ethyl terminated lactic acid oligomers having no less than 2 and no more than 10 units of lactic acid;

said material being characterized by having plastic malleability substantially without memory combined with low swelling.

4. The bioresorbable composition of claim 3, wherein the amount of plasticizer ranges from about 5 to 25% by weight of said composition.

5. The bioresorbable material of claim 1, wherein said crystalline polymer ranges from about 5 to 40% by weight of said material.

6. The bioresorbable composition of claim 1, wherein the amount of plasticizer ranges from about 5 to about 25% by weight of said composition.

7. The bioresorbable material of claim 6, wherein the plasticizer is at least one citrate ester, and the proportion of plasticizer ranges from about 9 to about 17% by weight of said material.

8. The bioresorbable material of claim 6, wherein said amorphous polymer is selected from at least one of the group consisting of poly-d,l-lactide and copolymers of poly-d-l-lactide and poly-l-lactide, the plasticizer is at least one ethyl-terminated lactic acid oligomer, and said plasticizer comprises about 20% by weight of said material.

9. The bioresorbable material of claim 6, wherein said material comprises about 76% by weight poly-d,l-lactide, 10% by weight poly-l-lactide as polymers, and 14% by weight acetyltri-n-butyl citrate as said plasticizer.

10. The bioresorbable material of claim 8, wherein said material comprises about 75% by weight poly-d, l-lactide and 10% by weight polycaprolactone as polymers, and 15% by weight acetyltri-n-butyl citrate as said plasticizer.

11. The bioresorbable material of claim 4, wherein said material comprises about 80% by weight poly-d,l-lactide, and 20% by weight of at least one ethyl-terminated oligomer of lactic acid as plasticizer.

12. The article of claim 2, wherein said crystaline polymer ranges from about 5 to 40% by weight of said material.

13. The article of claim 2, wherein the amount of plasticizer ranges from about 5 to about 25% by weight of the bioresorbable material.

14. The article of claim 13, wherein said amorphous polymer is selected from at least one of the group consisting of poly-d-l-lactide and copolymers of poly-d,l-lactide and poly-l-lactide, based on polylactic acid and said plasticizer is at least one citrate ester, and that the proportion of plasticizer ranges from about 9 to about 17% by weight of the said bioresorbable material.

15. The article of claim 13, wherein said amorphous polymer is selected from at least one of the group consisting of poly-d,l-lactide and copolymers of poly-d-l-lactide and poly-l-lactide, the plasticizer is at least one ethyl-terminated lactic acid oligomer and said plasticizer amounts to about 20% by weight of said bioresorbable material.

16. The article of claim 13, wherein said bioresorbable material comprises about 76% by weight poly-d,l-lactide and 10% by weight poly-l-lactide as polymers, and 14% by weight acetyltri-n-butyl citrate as said plasticizer.

17. The article of claim 2, wherein said article comprises a medical device comprising apertures formed by perforating.

18. Bioresorbable material adaptable for medical use comprising a bioresorbable polymer comprising about 75% by weight of said material of amorphous poly-d,l-lactide, and about 10% by weight of polycaprolactone, as polymers, and about 15% by weight acetyltri-n-butyl citrate as a plasticizer, said material being characterized by having plastic malleability substantially without memory combined with low swelling.

19. An article of manufacture adaptable for medical use made from a bioresorbable material comprising about 75% by weight amorphous poly-d,l-lactide and about 10% by weight of polycaprolactone as polymers, and about 15% by weight acetyltri-n-butyl citrate as a plasticizer, said material being characterized by having plastic malleability substantially without memory combined with low swelling.

20. An article of manufacture adaptable for medical use made from a bioresorbable material comprising about 80% by weight amorphous poly-d,l-lactide, and about 20% by weight of at least one ethyl-terminated oligomer of lactic acid as a plasticizer, said material being characterized by having plastic malleability substantially without memory combined with low swelling.

21. The article of claim 19 wherein said article comprises a medical device comprising apertures formed by perforating, wherein said apertures have a minimum transverse dimension of 10 µm.

22. The article of claim 21 wherein the total area of said apertures is at least 6%.

23. The article of claim 21, wherein said apertures are spaced at a center to center distance ranging from about 700 µm to 150 µm.

* * * * *

UNITED STATES PATENT AND TRADEMARK OFFICE
CERTIFICATE OF CORRECTION

PATENT NO. : 5,525,646
DATED : June 11, 1996
INVENTOR(S) : LUNDGREN et al.

It is certified that error appears in the above-indentified patent and that said Letters Patent is hereby corrected as shown below:

Column 4, lines 8,9, after "Mathisen et al" should read with no new paragraph;
Column 6, line 64, "I-PLA/50" should be --I-PLA/15--;
Column 13, line 7, delete "based on polylactic acid".

Signed and Sealed this

Twenty-sixth Day of November 1996

Attest:

BRUCE LEHMAN

Attesting Officer

Commissioner of Patents and Trademarks